United States Patent
Pech

(10) Patent No.: US 9,078,716 B2
(45) Date of Patent: Jul. 14, 2015

(54) SURGICAL MID-FOOT COMPRESSION PIN

(71) Applicant: ZIMMER GMBH, Winterthur (CH)

(72) Inventor: Uwe Pech, Tuttlingen (DE)

(73) Assignee: Zimmer GmbH, Winterthur (CH)

(*) Notice: Subject to any disclaimer, the term of this patent is extended or adjusted under 35 U.S.C. 154(b) by 129 days.

(21) Appl. No.: 13/649,145

(22) Filed: Oct. 11, 2012

(65) Prior Publication Data

US 2014/0107714 A1 Apr. 17, 2014

(51) Int. Cl.
*A61B 17/86* (2006.01)
*A61B 17/72* (2006.01)

(52) U.S. Cl.
CPC ........... *A61B 17/863* (2013.01); *A61B 17/7225* (2013.01); *A61B 17/7291* (2013.01)

(58) Field of Classification Search
CPC .................................................... A61B 17/863
USPC ......... 606/300, 301, 304, 305, 308, 309, 311, 606/312, 315–318, 321
See application file for complete search history.

(56) References Cited

U.S. PATENT DOCUMENTS

| | | | | |
|---|---|---|---|---|
| 3,051,169 A | * | 8/1962 | Grath | 606/65 |
| 4,463,753 A | * | 8/1984 | Gustilo | 606/308 |
| 5,019,079 A | * | 5/1991 | Ross | 606/312 |
| 5,334,204 A | * | 8/1994 | Clewett et al. | 606/312 |
| 5,544,993 A | * | 8/1996 | Harle | 411/414 |
| 5,964,768 A | | 10/1999 | Huebner | |
| 6,030,162 A | | 2/2000 | Huebner | |
| 6,306,140 B1 | | 10/2001 | Siddiqui | |

FOREIGN PATENT DOCUMENTS

EP 2564799 B1 4/2014

OTHER PUBLICATIONS

International search report dated Dec. 12, 2012.

* cited by examiner

*Primary Examiner* — Anu Ramana
(74) *Attorney, Agent, or Firm* — Schwegman Lundberg & Woessner, P.A.

(57) ABSTRACT

A surgical mid-foot compression pin (1), includes a core region (2) having a drive, a front thread portion (6) having a front outer thread (7), a rear thread portion (9) having a rear outer thread (10), and a middle portion (8) arranged between the thread portions, the pitch of the front outer thread (S1) being greater than that of the rear outer thread (10) so as to achieve a compression. In accordance with the invention, the rear outer thread (10) has a conical sleeve contour, which tapers in the direction of the front end (3) of the compression pin (1).

17 Claims, 3 Drawing Sheets

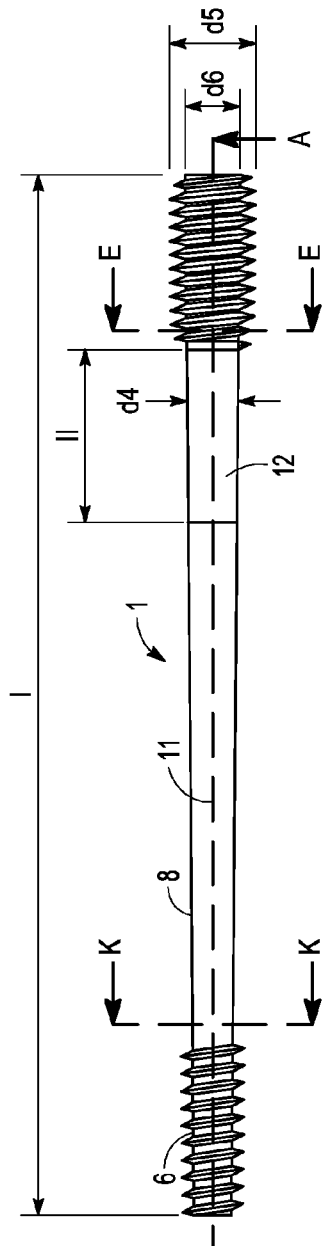
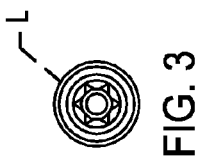
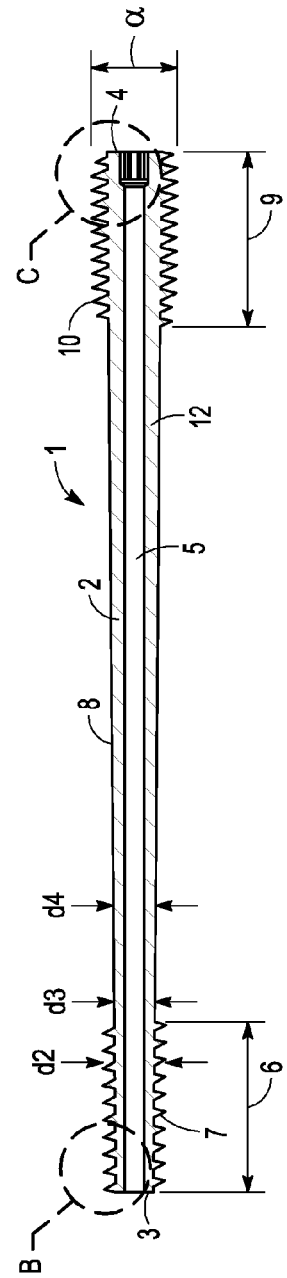

SURGICAL MID-FOOT COMPRESSION PIN

BACKGROUND OF THE INVENTION

The invention relates to a surgical mid-foot compression pin for implantation in the first cord of a human foot, said pin comprising a core region having a drive for screwing in and/or unscrewing the pin, a front thread portion having a front outer thread, a rear thread portion having a rear outer thread, and a middle portion arranged between the thread portions, the pitch of the front outer thread being greater than that of the rear outer thread to achieve a compression.

Inter alia, a mid-foot compression pin by Synthes GmbH is known on the market and is used for the treatment of mid-foot/hind foot collapse. The known compression pin has a stepped cylindrical sleeve contour and is provided with a front and a rear outer thread, wherein the pitch of the front outer thread is greater than that of the rear outer thread to achieve a compression. The known compression pin comprises a stepped core region, with an elongate rear cylinder portion and an axially adjoining front, diameter-reduced cylinder portion, wherein the rear cylindrically contoured outer thread is provided at the rear cylinder portion and, at the same time, a thread-free middle portion adjoins the rear outer thread. The known mid-foot compression pin could be improved in terms of its compressive action.

SUMMARY OF THE INVENTION

Proceeding from the above-mentioned prior art, the object of the invention is to disclose a surgical mid-foot compression pin having improved compressive action. It will be possible to anchor the compression pin easily and durably in the foot bones, and preferably to unscrew said compression pin again in a simple manner.

With a generic mid-foot compression pin, this object is achieved in particular by the features disclosed herein such that the rear outer thread has a conical sleeve contour, which tapers in the direction of the front end of the compression pin.

Advantageous developments of the invention are also disclosed in the dependent claims. All combinations of at least two features disclosed in the description, the claims and/or the figures fall within the scope of the invention. To avoid repetition, features disclosed in accordance with the device are also considered to be disclosed and claimable in accordance with the method. Features disclosed in accordance with the method are likewise considered to be disclosed and claimable as device features.

To improve the compression of foot bones penetrated by the mid-foot compression pin, the invention proposes providing the rear outer thread with a conical sleeve contour, wherein the conical sleeve contour of the rear outer thread tapers in the direction of a front end of the compression pin. It is particularly preferable if at least a maximum outer diameter of the rear outer thread is greater than a maximum outer diameter of the front outer thread, wherein a minimum outer diameter of the rear outer thread greater than the maximum outer diameter of the front outer thread is also additionally yet more preferable. Due to the conical sleeve contour of the rear outer thread, an improved compressive effect can surprisingly be achieved. In addition, automatic rotation of the compression pin in a direction in which said pin is screwed in can be reliably prevented due to the conical sleeve contour, and therefore the implantation position (fixing position) is much more defined than with known foot compression pins.

The surgical mid-foot compression pin according to the invention is suitable for insertion into the first (largest) cord of a human foot, wherein the compression pin is designed to be implanted or screwed into the foot in a retrograde manner via the talus, naviculars, cuneiforms and metatarsals. It is particularly expedient if, in accordance with a development, the compression pin has a through-hole (to be explained in greater detail further below) in the core region so as to receive a Kirschner wire, since this allows a revolutionary guided screwing-in of the compression pin with the aid of a targeting device via a Kirschner wire.

During the operation, the patient's foot is preferably supported laterally. It is not necessary to be able to reach the heel and inner foot due to the possibility for retrograde insertion. For implantation, guided via the Kirschner wire with the aid of a targeting device, a core hole for the compression pin is preferably drilled in the foot, in particular up to a distance of approximately 1 cm for example, before a distal fixing block. The required screw length can then preferably be read on a corresponding scale or on the targeting device in another manner and/or on a corresponding marking on the drill. The core hole drill is then preferably removed and a countersink for receiving the rear outer thread, which is preferably formed with an expanded diameter, is preferably milled by hand, in particular in the talus bone, by means of a countersink milling cutter. Once the core drill has been removed, in particular by means of reaming, the initially cylindrical bore is preferably contoured conically so as to cooperate optimally with the preferred shape of the compression pin according to the invention, which is conical at least over portions, so as to thus in turn achieve much greatly improved compression. A correspondingly dimensioned (matching) compression pin is then screwed in, preferably via the Kirschner wire, whereupon the wound can then be closed.

An assortment of compression pins of different length, in particular measuring 120 mm, 130 mm and 140 mm, is most preferably provided. It has proven to be particularly advantageous if the cylindrical core hole drill is designed or suitable for receiving at least one 2.0 Kirschner wire.

It has proven to be particularly advantageous if the pitch of the front thread portion exceeds the pitch of the rear thread portion by a value range between 0.2 and 0.6, preferably between 0.3 and 0.4. It is most expedient if the pitch of the front thread is 0.31 times greater than that of the rear outer thread. It is particularly expedient if the pitch of the front outer thread is selected from a value range between 1.8 and 2.2, preferably of 2.0, and/or the pitch of the rear outer thread is selected from a value range between 1.4 and 1.8, preferably of 1.59. With regard to a further advantageous embodiment of the invention, it has proven to be advantageous if the angle between two mutually opposed thread flanks of the front and/or rear outer thread is selected from a value range between 25° and 35°, preferably of approximately 30°. It is more preferable if the axial extension of the front outer thread portion and/or of the rear outer thread portion is at least 10 mm. The axial extension of the respective outer thread portion is most preferably selected from a value range between 10 mm and 30 mm, and is yet more preferably approximately 20 mm.

In principle, it is possible to provide not only the rear outer thread, but also the front outer thread, with a conical sleeve contour, wherein, in this case, it is preferable if the sleeve contours of the front and rear outer thread are part of a common (virtual) sleeve contour with a single (common) cone angle. However, it has proven to be particularly advantageous if the front outer thread does not have a conical sleeve contour, but a cylindrical sleeve contour. The core region is also preferably contoured cylindrically, and not conically, radially within the front outer thread. Due to the cylindrical sleeve contouring of the front outer thread, the compression pin is provided with greater stability, and therefore the risk of a possible bending of the front portion of the compression pin is counteracted. Durable, stable positioning is thus enabled on the whole.

The cone angle (angle between two diametrically opposed virtual sleeve lateral surfaces) of the sleeve contour of the rear outer thread is preferably selected from an angular range between approximately 0.5° and approximately 4°, preferably between approximately 1° and 3°, and is more preferably approximately 2°.

Particularly good stability of the connection between the compression pin and foot bone as well as an optimised compressive effect can be achieved since the preferably thread-free middle portion arranged between the two outer thread portions is likewise contoured conically, at least over portions, and tapers in the direction of the front end of the compression pin, similarly to the sleeve contours of the outer thread. Due to the at least partially conical design of the middle portion, preferably at least in a front region, or alternatively at least approximately over its entire longitudinal extension, it is also possible to compress foot bone pieces, even if an intermediate bone portion has to be removed, since the position of the remaining bone pieces is predetermined or defined on the basis of the shape of the middle portion, which is conical at least over portions, or of the corresponding conical bore. It is most preferable if the middle portion is not continuously conically contoured (which is alternatively possible, as mentioned), but if a cylindrically contoured region is provided between a conically contoured (front) middle portion and the rear outer portion and preferably has an axial extension from a value range between 10 mm and 30 mm, preferably of approximately 20 mm. It is particularly expedient if the diameter of this cylinder portion is at least approximately 6 mm. The aforementioned cylinder portion most preferably forms the largest diameter region or has the largest diameter of the middle portion, beyond which the outer thread projects. The cylindrical design of a sub-portion of the middle portion makes the compression pin more stable, whereby said pin is better secured against possible bending, and corresponding forces and torques can be better counteracted.

Instead of a continuously conical contouring of the core region, it is particularly advantageous if the preferably integral or one-piece core region has a conical portion arranged further to the front and a rear conical portion, which are interconnected integrally via a cylinder portion, wherein the cylinder portion is preferably part of the middle portion and yet more preferably is located between a front conical portion of the middle portion and the rear outer thread portion. It is most expedient if the foremost portion of the core region, which adjoins the conical front portion of the middle portion, is cylindrically contoured.

The two outer threads preferably protrude (clearly) beyond a respective adjacent portion of the middle portion in the radial direction so as to thus provide improve anchoring in the foot bone, and thus ultimately improved compression, compared to known compression pins. It has proven to be particularly expedient if the rear outer thread, at least in a portion of a greatest diameter of the preferably, but not necessarily, conical middle portion, protrudes by a value from a value range (measured in a radial direction) between approximately 2.0 and approximately 7.0 mm, preferably between approximately 3.0 and approximately 5.0 mm, more preferably of approximately 3.3 mm. It is particularly expedient if the rear outer thread protrudes beyond the greatest diameter of the middle portion over the majority of the longitudinal extension of the rear outer thread by a distance from the above-mentioned value range, wherein this greatest diameter of the middle portion is more preferably formed by the above-mentioned cylinder portion. Alternatively, or preferably in addition, to the previously explained embodiment of the rear outer thread, it is preferable if the front outer thread, preferably over the majority of its axial extension, protrudes beyond at least a smallest diameter of the middle portion by a distance (measured in a radial direction) from a value range between approximately 1.0 mm and approximately 4.0 mm, preferably between 1.5 mm and approximately 2.5 mm.

To achieve optimal and durable retention in the bone as well as a good level of durable compression associated therewith, it has proven to be particularly advantageous if the depth of grooves in the front outer thread and/or the rear outer thread is constant over at least 75%, preferably at least 85%, preferably over at least 95%, of the axial extension of the corresponding outer thread. In other words, it is thus preferable if the core region arranged radially within the thread grooves is conically contoured in the rear outer thread (similarly to the sleeve contour of this outer thread), in particular with the cone angle of the rear outer thread.

The cone angle of the conical part of the middle portion preferably corresponds to the cone angle of the sleeve contour of the rear outer thread.

In accordance with a development of the invention, so as to enable the compression pin to be screwed in in a facilitated manner or to dispense with a separate thread cutting step before the compression pin is screwed in, the front outer thread is preferably assigned front furrowing and/or cutting means and/or the rear outer thread is preferably assigned furrowing and/or cutting means for automatic thread forming. The furrowing and/or cutting means may also be used, in particular simultaneously, to enable facilitated release of the compression pin, since the furrowing and/or cutting means automatically cut free bone, cartilage or other tissue that may have grown over time. A larger, more complex operative intervention, associated with more complications, for removing the compression pin can be dispensed with due to the embodiment according to the development. It is sufficient to open the foot only in a rear region. Furrowing and/or cutting means are preferably provided integrally in the corresponding outer thread. In particular since corresponding cutting edges acting in a circumferential direction are provided. A plurality of cutting edges spaced in particular uniformly in the circumferential direction are preferably formed on at least one of the outer threads, in particular at an end arranged in the direction in which the compression pin is screwed in. These may also enable facilitated release of the compression pin.

As has already been mentioned, it is particularly expedient if a central through-opening, for passing through a Kirschner wire to guide the compression pin as it is screwed in and/or unscrewed, is provided in the solid core region, preferably formed of titanium, of the compression pin, which is integral in particular. The diameter is preferably selected from a value range between 2.05 and 2.5 mm, and in any case is preferably more than 2.0 mm. The inner diameter is preferably approximately 2.2 mm.

The invention also leads to a system comprising a previously described compression pin formed in accordance with the concept of the invention and a targeting device as a positioning aid when implanting the compression pin. The targeting device is preferably designed to receive different guides, for example for a Kirschner wire or for a core hole drill, wherein these guides are yet more preferably fixable by means of a bayonet closure.

BRIEF DESCRIPTION OF THE DRAWINGS

Further advantages, features and details of the invention will emerge from the following description of preferred exemplary embodiments and from the drawings, in which:

FIG. 1 shows a side view of a preferred exemplary embodiment of a surgical mid-foot compression pin according to the invention, FIG. 2 shows a longitudinal sectional view of the compression pin according to FIG. 1 along the line of section A-A, FIG. 3 shows a rear view of the compression pin according to FIG. 1, FIG. 4 shows a front view of the compression pin according to FIG. 1.

DETAILED DESCRIPTION

Figure 5:
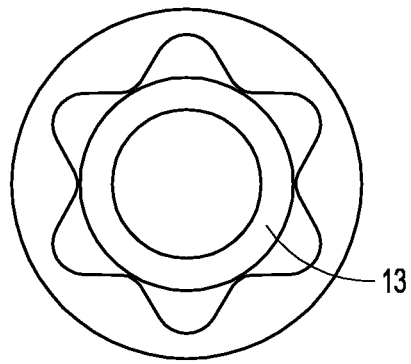
FIG. 5 shows an enlargement of the detail L according to FIG. 3.
Figure 6:
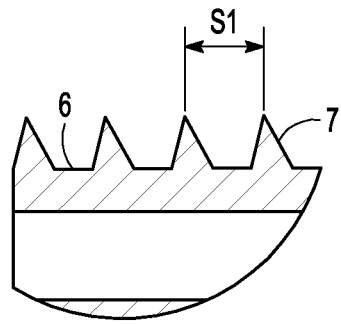
FIG. 6 shows an enlargement of the detail B from FIG. 2.

A surgical mid-foot compression pin 1, referred to hereinafter as a compression pin 1, is illustrated in the figures. This pin has a length 1 of 120 mm in the exemplary embodiment shown, wherein compression pins of different length are combined in an assortment. The compression pin 1 comprises a solid core region 2, which extends axially from a front end 3 illustrated to the left in the drawing plane to a rear end 4 of the compression pin 1 arranged to the right in the drawing plane. The solid core region 1 is provided with a through-opening 5 to receive a 2.0 Kirschner wire, wherein the cylindrical through-opening 5 has a diameter d1 of 2.2 mm in the exemplary embodiment shown.

A front thread portion 6 adjoins the front end 3 axially and has an axial extension of 20 mm in the exemplary embodiment shown. The front thread portion 6 has a front outer thread 7, which connects radially to the cylindrical core region 2 in the front region. The front outer thread 7 has a pitch of 2.0 mm in the exemplary embodiment shown and is provided with a cylindrical sleeve contour. In this case the front outer thread 7 has an axially continuous outer diameter d2 of 7 mm. The front outer thread 7 projects beyond a smallest outer diameter of a middle portion 8 axially adjoining the front thread portion 6. This smallest outer diameter d3 is approximately 4.5 mm in the exemplary embodiment shown.

The middle portion 8 is thread-free and extends axially between the front (cylindrical) thread portion 6 and a rear thread portion 9, which likewise has an axial extension of 20 mm and which is provided with a rear outer thread 10. The middle portion 8 is divided into a front, conically contoured cone portion 11 and an axially adjoining rear cylinder portion 12, wherein the cylinder portion has an axial extension 11 of 20 mm in the exemplary embodiment shown and an outer diameter d4 of mm. The outer diameter d4 simultaneously constitutes the greatest diameter of the middle portion 8. It can be seen that the middle portion 8 is conically contoured over more than three quarters of its axial extension.

The rear outer thread 10 has a conical sleeve contour having a cone angle α of 2° in the exemplary embodiment shown. The depth of the rear outer thread 10 is constant over practically its entire axial extension in the exemplary embodiment shown, since the core region is also conically contoured in the region of the rear thread portion 9 and has a cone angle of 2° corresponding to the cone angle α. As can be seen from FIG. 1, the maximum outer diameter d5 of the compression pin 1, and simultaneously of the rear outer thread 10, is 10 mm in the region of the rear end 4. In this region, the outer thread thus protrudes beyond the greatest diameter d4 of the middle portion by 4 mm and beyond the core region by 3.29 mm, which has a diameter d6 of 6.71 mm in this region.

Figure 7:
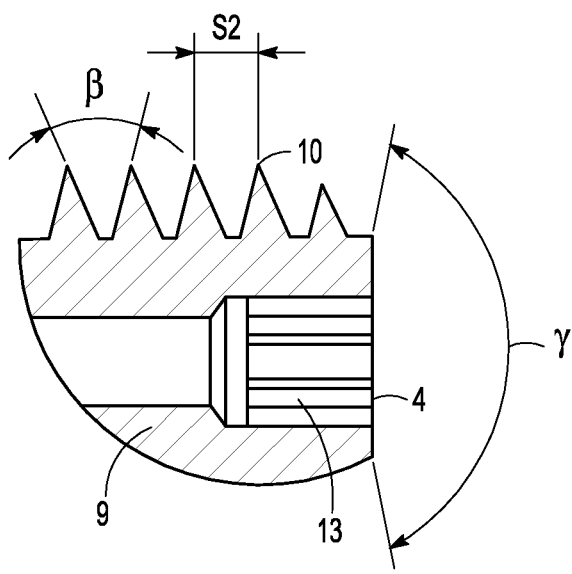
FIG. 7 shows an enlargement of the detail C from FIG. 2.

It can be seen from FIG. 7 that the pitch s2 of the rear outer thread 10 is 1.59 in the exemplary embodiment shown. An angle β between two mutually opposed thread flanks of the rear outer thread is 30°. It can also be seen that the rear end of the compression pin 1 is concavely contoured at the end face and has an angle of curvature γ of 163°. Different angles of curvature can be formed alternatively. A drive 13, which is illustrated in section in FIG. 7 and which is located in the region of the rear end 4, is shown in plan view in FIG. 5. It can be seen that the drive 13 is formed as a torx drive by way of example.

Figure 8:
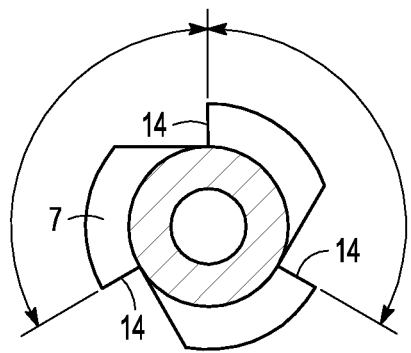
FIG. 8 shows a cross-sectional view along the line of section K-K according to FIG. 1.
Figure 9:
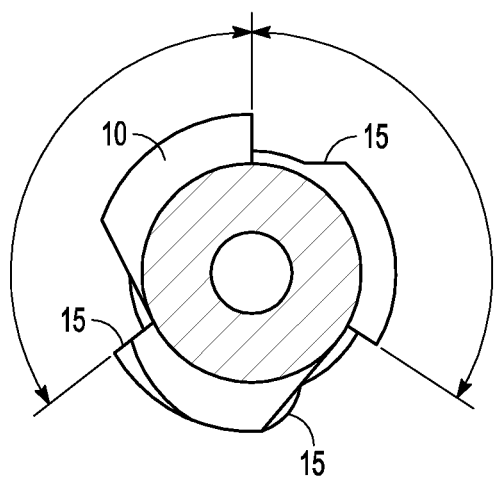
FIG. 9 shows a cross-sectional view along the line of section E-E according to FIG. 1.

Three cutting edges 14, spaced uniformly in the circumferential direction, of the front thread 6 designed as a self-cutting thread can be seen in FIG. 8. The cutting edges form cutting means so as to automatically form a counter thread as the compression pin is screwed into the bone. Similarly, the rear outer thread 10 is assigned rear cutting means in the form of three cutting edges 15 spaced uniformly in the circumferential direction, wherein cutting edges for each direction of rotation are provided in both cutting means so as to also enable facilitated release of the compression pin 1.

The invention claimed is:

1. A surgical mid-foot compression pin, comprising: a front threaded portion including a distal end of the compression pin, the front threaded portion comprising a front outer thread; a rear threaded portion including a proximal end of the compression pin, the rear threaded portion comprising a rear outer thread; an unthreaded middle portion arranged between the front and rear threaded portions; and a drive interface extending from the proximal end into the compression pin, the compression pin having a longitudinal axis extending between the proximal end and the distal end; wherein a pitch of the front outer thread is greater than a pitch of the rear outer thread in order to achieve a compression; wherein the rear outer thread has a conical contour that tapers along the longitudinal axis, in a direction from the proximal end to the distal end of the compression pin; and wherein at least part of the middle portion is contoured conically at least over portions thereof, and tapers along the longitudinal axis in the direction from the proximal end to the distal end of the compression pin.

2. The compression pin according to claim 1, wherein the front outer thread has a cylindrical contour.

3. The compression pin according to claim 1, wherein the conical contour of the rear outer thread defines a cone angle between 0.5° and 4°.

4. The compression pin according to claim 3, wherein the cone angle is between 1° and 3°.

5. The compression pin according to claim 4, wherein the cone angle is 2°.

6. The compression pin according to claim 1, wherein the front outer thread and the rear outer thread each define an outer diameter that is greater than an outer diameter of the middle portion.

7. The compression pin according to claim 6, wherein the rear outer thread extends in the radial direction by a distance between 2.0 mm and 7.0 mm beyond a greatest diameter of the middle portion, and wherein the front outer thread extends in the radial direction by a distance between 1.0 mm and 4.0 mm beyond a smallest diameter of the middle portion.

8. The compression pin according to claim 7, wherein the rear outer thread extends in the radial direction by a distance between 3.0 mm and 5.0 mm beyond the greatest diameter of the middle portion.

9. The compression pin according to claim 7, wherein the front outer thread extends in the radial direction by a distance between 1.5 mm and 2.5 mm beyond the smallest diameter of the middle portion.

10. The compression pin according to claim 1, wherein a thread depth of at least one of the front outer thread and the rear outer thread is constant over at least 75% of an axial length of the corresponding outer thread, the axial length defined along the longitudinal axis of the compression pin.

11. The compression pin according to claim 10, wherein the thread depth of the at least one of the front outer thread and the rear outer thread is constant over at least 85% of the axial length of the corresponding outer thread.

12. The compression pin according to claim 10, wherein the thread depth of the at least one of the front outer thread and the rear outer thread is constant over at least 95% of the axial length of the corresponding outer thread.

13. The compression pin as claimed in claim 1, wherein at least one of the front outer thread and the rear outer thread includes a furrowing element or a cutting element for automatic thread forming in a foot bone as the compression pin is screwed into or unscrewed from a bore in the foot bone.

14. The compression pin according to claim 1, further comprising a central through-opening configured for receiving a Kirschner wire to guide the compression pin as it is screwed into or unscrewed from a foot bone.

15. A system, comprising the compression pin of claim 1 and a targeting device for implantation of the compression pin.

16. The compression pin according to claim 1, wherein the middle portion has an axial length defined along the longitudinal axis of the compression pin, and wherein the middle portion is conically tapered over a majority of the axial length.

17. The compression pin according to claim 1, wherein the middle portion includes an unthreaded cylindrical portion.

* * * * *